(12) United States Patent
Doll et al.

(10) Patent No.: US 9,398,920 B2
(45) Date of Patent: Jul. 26, 2016

(54) SURGICAL INSTRUMENT SYSTEM

(75) Inventors: Frank Doll, Talheim (DE); Christian Walter, Emmingen-Liptingen (DE); Walter Roesch, Donaueschingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 717 days.

(21) Appl. No.: 11/269,983

(22) Filed: Nov. 9, 2005

(65) Prior Publication Data

US 2006/0089527 A1    Apr. 27, 2006

Related U.S. Application Data

(63) Continuation of application No. PCT/EP2005/004196, filed on Apr. 20, 2005.

(30) Foreign Application Priority Data

Apr. 30, 2004   (DE) .......................... 10 2004 021 713

(51) Int. Cl.
    *A61B 1/00*      (2006.01)
    *A61B 17/32*     (2006.01)
    (Continued)

(52) U.S. Cl.
    CPC .............. *A61B 17/32002* (2013.01); *A61B 1/31* (2013.01); *A61B 17/29* (2013.01);
    (Continued)

(58) Field of Classification Search
    CPC ............. A61B 17/29; A61B 17/32002; A61B 17/32053; A61B 2017/320024; A61B 2017/3445; A61B 1/015; A61B 1/31; A61B 2217/005; A61B 2217/007; A61M 1/0062

USPC ................... 606/170, 180, 205, 206, 207, 34; 600/105, 567, 153, 134, 140, 104
    See application file for complete search history.

(56) References Cited

U.S. PATENT DOCUMENTS 2,028,635 A    1/1936  Wappler
4,132,227 A *  1/1979  Ibe ................................ 600/105
(Continued)

FOREIGN PATENT DOCUMENTS

DE       74 42 379     4/1975
DE       44 40 035     5/1996
(Continued)

OTHER PUBLICATIONS

PCT International Search Report, Oct. 8, 2005, 3 pages.

*Primary Examiner* — Corrine McDermott
*Assistant Examiner* — Sarah Simpson
(74) *Attorney, Agent, or Firm* — Whitmyer IP Group LLC

(57) ABSTRACT

The invention relates to a surgical instrument system encompassing a morcellator with a hollow shaft on whose distal end a cutting blade is configured, as well as a gripping instrument with a shaft on whose distal end a tool consisting of at least two jaw members and on whose proximal end a handle consisting of at least two gripping members is configured to activate the tool, in such a way that the gripping instrument can be inserted into the hollow shaft of the morcellator so that it can slide in the longitudinal direction of the morcellator shaft. To ensure versatile application along with simple structure, it is proposed with the invention that the morcellator with the insertable gripping instrument can be inserted into a hollow shaft of an additional medical instrument, in particular a resectoscope, and that an additional irrigation and/or suction canal is configured between the shaft of the morcellator and the inside of the hollow shaft of the additional medical instrument.

15 Claims, 3 Drawing Sheets

(51) Int. Cl.

| | | |
|---|---|---|
| *A61B 1/31* | (2006.01) | |
| *A61B 17/29* | (2006.01) | |
| *A61B 1/015* | (2006.01) | |
| *A61B 17/3205* | (2006.01) | |
| *A61B 17/34* | (2006.01) | |
| *A61M 1/00* | (2006.01) | |

(52) U.S. Cl.
CPC .......... *A61B 1/015* (2013.01); *A61B 17/32053* (2013.01); *A61B 2017/3445* (2013.01); *A61B 2217/005* (2013.01); *A61B 2217/007* (2013.01); *A61M 1/0062* (2013.01)

(56) References Cited

U.S. PATENT DOCUMENTS

| | | | | |
|---|---|---|---|---|
| 4,706,656 | A | 11/1987 | Kuboto | 128/6 |
| 5,084,057 | A * | 1/1992 | Green et al. | 606/142 |
| 5,488,958 | A | 2/1996 | Topel et al. | 128/754 |
| 5,618,296 | A * | 4/1997 | Sorensen et al. | 606/180 |
| 5,797,939 | A * | 8/1998 | Yoon | 606/167 |
| 5,807,240 | A * | 9/1998 | Muller et al. | 600/135 |
| 5,814,044 | A * | 9/1998 | Hooven | 606/48 |
| 5,984,939 | A * | 11/1999 | Yoon | 606/170 |
| 6,039,748 | A * | 3/2000 | Savage et al. | 606/180 |
| 6,113,594 | A * | 9/2000 | Savage | 606/41 |
| 6,156,049 | A * | 12/2000 | Lovato et al. | 606/170 |
| 6,468,228 | B1 | 10/2002 | Topel et al. | 600/567 |
| 6,537,273 | B1 * | 3/2003 | Sosiak et al. | 606/41 |
| 6,712,759 | B2 * | 3/2004 | Muller | 600/156 |
| 6,746,395 | B2 * | 6/2004 | Brommersma et al. | 600/105 |
| 2002/0183589 | A1* | 12/2002 | Brommersma et al. | 600/105 |
| 2005/0070892 | A1* | 3/2005 | Ciarrocca | 606/46 |
| 2006/0047185 | A1* | 3/2006 | Shener et al. | 600/156 |
| 2006/0189920 | A1* | 8/2006 | Seeh | 604/22 |

FOREIGN PATENT DOCUMENTS

| | | |
|---|---|---|
| DE | 199 08 721 | 9/2000 |
| DE | 100 09 020 | 9/2001 |
| DE | 202 04 691 | 7/2002 |
| DE | 101 56 313 | 6/2003 |
| DE | 695 30 257 | 11/2003 |
| EP | 0 621 008 | 10/1994 |
| WO | WO 99/07295 | 2/1999 |
| WO | WO 00/48505 | 8/2000 |

* cited by examiner

SURGICAL INSTRUMENT SYSTEM

CROSS-REFERENCE TO RELATED APPLICATIONS

This application is a continuation of pending International Patent Application No. PCT/EP2005/004196 filed on Apr. 20, 2005 designating the United States and claiming priority from German Patent Application No. 10 2004 021 713.0 filed on Apr. 30, 2004.

FIELD OF THE INVENTION

The invention relates to a surgical instrument system that includes a morcellator with a hollow shaft on whose distal end a cutting blade is configured as well as a gripping instrument with a shaft, having on its distal end a tool consisting of at least two jaw members and on its proximal end a handle for activating the tool consisting of at least two gripping members, in such a way that the gripping instrument can be inserted into the hollow shaft of the morcellator in the longitudinal direction of the morcellator shaft.

BACKGROUND OF THE INVENTION

In endoscopic surgical interventions, such as in laparoscopy, it is customary to create several points of access to the operating area in order to convey medical instruments, such as for instance cutting and/or gripping instruments for performing the operation, to the operating area by at least one means of access and to convey an observation unit, such as an endoscope for observing and guiding the operation, by at least one additional means of access.

However, if the operating area is very limited and small, as is the case for instance in operations of the bladder, it is impossible to convey the observation unit into the operating area by a separate means of access.

For these purposes, DE 202 04 691 U1, for instance, teaches inserting the optical observation unit together with a morcellator into the hollow shaft of an additional medical instrument, such as a resectoscope. In this instrument configuration known from the art, the optical observation unit consisting of a viewing canal and light cables is structured in the shape of a sickle and positioned in the resectoscope contiguous to the interior wall of the resectoscope shaft in order to create the largest possible working passage for the morcellator that is likewise inserted into the hollow resectoscope shaft. Although this instrument arrangement known in the art has proved itself in practice, it is also true that the arrangement of the optical observation unit and of the morcellator in the resectoscope shaft requires a small diameter for the morcellator cutting blade. It is therefore a disadvantage of this known arrangement that using a small cutting blade in morcellating large tissue areas requiring morcellation can last quite a long time.

In addition, WO 99/07295 A1 teaches a system for surgical removal of tissue consisting of a morcellator and gripping instrument that can be inserted into the hollow shaft of the morcellator. For operating, the morcellator is inserted directly into the artificial bodily opening so that the external mantle surface of the morcellator shaft provides insulation for the patient.

SUMMARY OF THE INVENTION

Consequently, it is the object of the invention to create a surgical instrument system that consists of a morcellator and a gripping instrument, is of simple construction, and can be used in a variety of ways.

This object is fulfilled in that the morcellator with its insertable gripping instrument can be inserted into a hollow shaft of an additional medical instrument, in particular a resectoscope, and that an additional irrigation and/or suction canal is configured between the shaft of the morcellator and the inside of the hollow shaft of the additional medical instrument.

Because of the inventive use of an additional hollow-shaft instrument, into which the morcellator with the gripping instrument can be inserted, the range of application of the instrument system can be considerably widened, because now it is possible also to use structural reciprocal effects between the morcellator and the other hollow-shaft instrument. This additional canal, in practical operation, serves preferably as a reverse-flow canal.

Therefore the surgical instrument system configured in this manner is distinguished in that, thanks to the structural design of the morcellator shaft and/or of the interior of the hollow shaft of the additional medical instrument, an additional irrigation or suction canal can be configured between the shaft of the morcellator and the interior of the hollow shaft of the additional medical instrument, and this canal permits an improved use of the inventive surgical instrument system.

According to a first practical embodiment, to configure the additional irrigation and/or suction canal the distal end of the hollow shaft of the additional medical instrument is shaped to form an inward arc. The bending of the distal end of the hollow shaft is advantageous in addition in order to ensure non-traumatic insertion of the shaft into the operating area.

With a second embodiment of the invention it is proposed that, to form the additional irrigation and/or suction canal, at least one longitudinal groove is configured in the casing surface of the shaft of the morcellator.

According to a third practical embodiment of the invention, the additional irrigation and/or suction canal can be configured so that the shaft of the morcellator, set off from the distal-side cutting blade, has a caliber indentation that reduces the diameter of the shaft.

To insulate the additional irrigation and/or suction canal on the proximal side, it is proposed that the additional irrigation and/or suction canal is insulated from the interior of the hollow shaft of the additional medical instrument by means of a layer, in particular a layer of Teflon.

It is further proposed with the invention that the gripping instrument is additionally equipped with an optical observation unit as well as at least one irrigation and/or suction canal, in such a way that the at least one irrigation and/or suction canal is positioned inside the optical observation unit. Because of the displacement of the optical observation unit and at least one irrigation and/or suction canal onto the gripping instrument and thus into the interior of the morcellator shaft, the freedom of movement of the morcellator is increased and it becomes possible to increase the morcellator diameter and thereby the cutting area.

During insertion of the morcellator into the operating area it can occur that tissue that is not to be treated comes in contact with the cutting blade of the morcellator shaft and is injured by the sharp cutting blade. Therefore, according to another embodiment of the invention, mounted on the gripping instrument is a cutting blade shield configured as a thickened area, which is adjacent at least to the cutting blade of the morcellator in form-locking connection, that is, radially flush on the inside of the shaft of the morcellator. Because of this form-locking adjacent placement on the inside of the cutting blade and the at least flush locking of the cutting blade guard with the cutting blade, injuries while inserting the morcellator are prevented.

This thickened area serving as cutting blade guard is preferably positioned on the proximal side of the shaft of the gripping instrument at a distance from the tool.

According to a preferred embodiment of the invention, the gripping tool that can be inserted into the morcellator shaft is a gripping pincer equipped with two movable jaw members for grasping and removing morcellated tissue.

To facilitate handling of the gripping tool for the operator, it is further proposed with the invention that the jaw members can be fixed in their relative position toward one another so that the operator, for instance, can released the gripping members of the handle without, in the process, losing the portion of tissue grasped by the jaw members.

The jaw members can be rotated with respect to one another either in pre-established angle positions or at any position of choice, and the jaw members can be mechanically fixed by means of the handle, the jaw members themselves, or a push-pull rod connecting the jaw members and the handle to one another.

To prevent the jaw members of the tool operating in the gripping position on the distal side outside the morcellator shaft from coming in contact with the cutting blade of the morcellator shaft and damaging it when the gripping tool is drawn into the morcellator shaft, it is proposed in a practical embodiment of the invention that the angle of rotation of the jaw members to one another when the gripping tool is drawn into the morcellator shaft should be restricted in such a manner that the jaw members of the tool should be capable of being drawn into the shaft without touching.

Finally, it is proposed with the invention that the hollow shaft of the morcellator should be insulatable from the environment by means of a double-layer insulating arrangement, in such a way that an insulation of the double-insulating arrangement is preferably configured as a ring insulating disc for insulation from the gripping instrument that can be inserted into the shaft and the other insulation of the double-insulating arrangement is preferably configured as a cross-slit insulation that insulates the interior lumen of the shaft when the gripping instrument is withdrawn.

Further characteristics and advantages of the invention can be seen from the description of the related illustration, in which two embodiments of an inventive surgical instrument system are depicted in merely exemplary form.

DETAILED DESCRIPTION OF THE INVENTION

Figure 1:
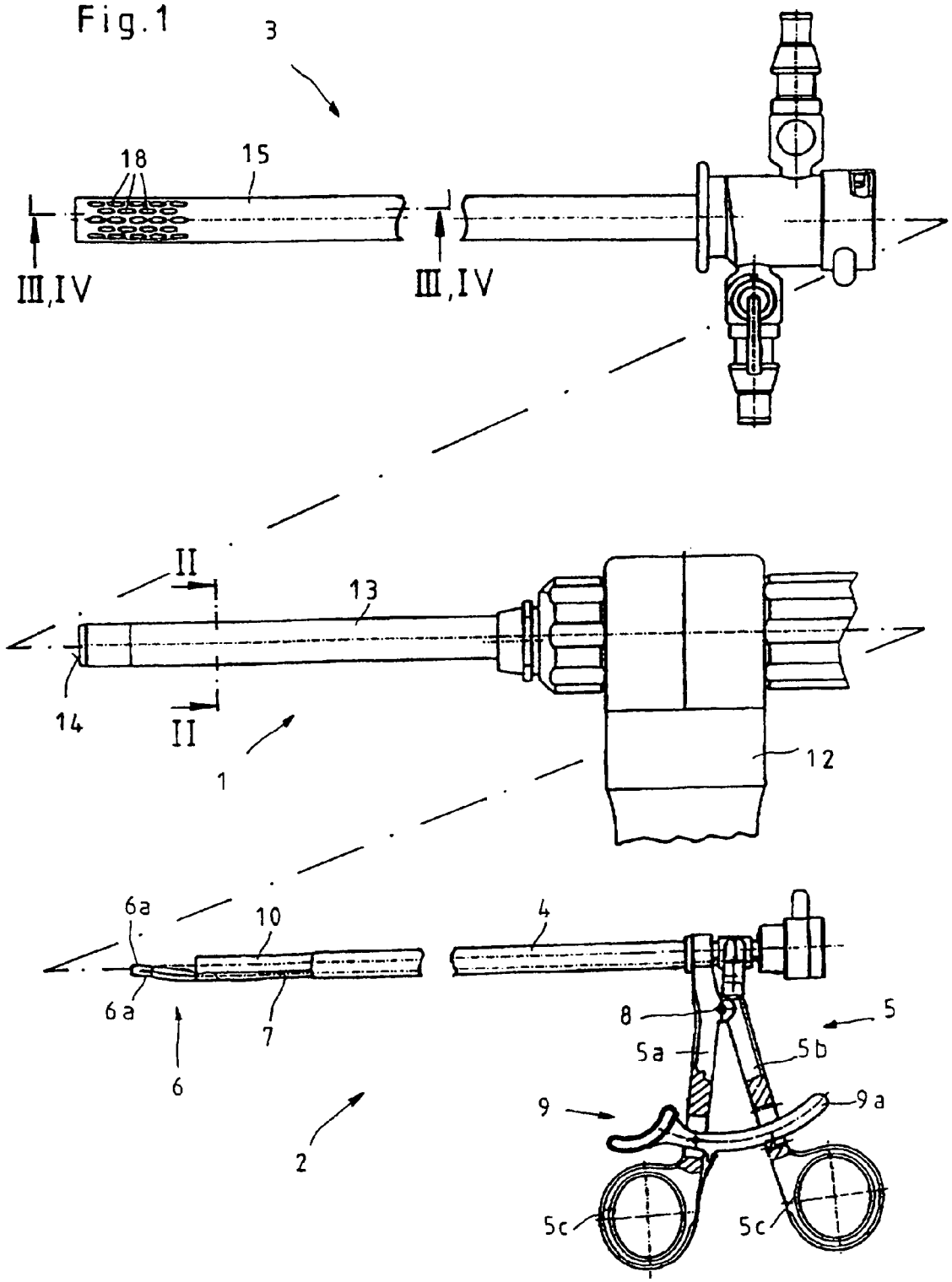
FIG. 1 shows a schematic side view of an inventive surgical instrument system inserted into a resectoscope.

The surgical instrument system depicted in FIG. 1 consists of a morcellator 1, a gripping instrument 2 that can be inserted into the morcellator 1, and a resectoscope 3 for inserting the morcellator 1 equipped with the gripping instrument 2.

The gripping instrument 2 configured as a gripping pincer consists essentially of a hollow shaft 4, on whose proximal end a handle 5 is positioned, which handle 5 consists of a rigid gripping member 5a and a gripping member 5b that can rotate with respect to the rigid gripping member 5a. On the distal end of the shaft 4, a tool 6 is positioned which includes two jaw members 6a that can rotate with respect to one another in the depicted embodiment. To activate the tool 6, the handle 5 and the jaw members 6a f the tool 6 are connected to one another by means of a push-pull rod positioned inside the shaft.

To ensure secure gripping of the gripping members 5a, 5b of the handle 5, these members have finger loops 5c on their free ends. In the illustrated embodiment the gripping members 5a, 5b, which can rotate with respect to one another around a rotation axis 8, can be fixed in place in the rotated position by means of a stop mechanism 9. Because of this fixing of the gripping members 5a, 5b to one another, the jaw members 6a, which are connected with the gripping members 5a, 5b by means of the push-pull rod 7 are also immediately fixed in their corresponding angle position with respect to one another.

The stop mechanism 9, which fixes the tool 6 in position, allows the operator to continue securely holding a tissue portion grasped by the jaw members 6a even when he no longer activates the handle 5, thus clearly facilitating his work.

In addition to the illustrated embodiment, in which the stop mechanism 9 is configured as a sickle-shaped notching rod 9a positioned on the gripping member 5a of the handle 5, which engages with notching teeth, not shown in the illustration, on the gripping member 5b of the handle 5, it is also possible of course to configure a stop mechanism 9 in the area of the jaw members 6a or of the push-pull rod 7 in order to fix the jaw members in their angle position with respect to one another, in such a way that the jaw members can be fixed with respect to one another either in pre-established angle positions or else in any freely selected position.

As a special feature, the gripping instrument 2 includes an optical observation unit 10 positioned in the shaft 4, by means of which unit it is possible directly to observe and conduct the operation with the tool 6. The optical observation unit 10 itself consists of at least one viewing canal and at least one light cable.

In addition to the optical observation unit 10, the gripping instrument 2 has at least one irrigation and/or suction canal 11 positioned in the shaft 4, to ensure good lighting and visual conditions in the operating area and to allow clear oversight of the operating process. The at least one irrigation and/or suction canal 11 can be attached to an external irrigation-suction unit.

Figure 2:
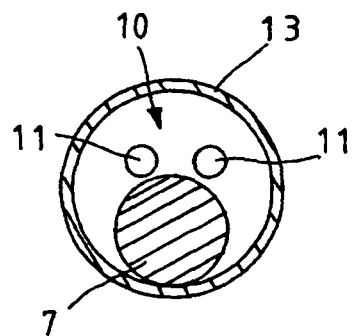
FIG. 2 shows an enlarged schematic cross-section along the section line II-II according to FIG. 1 with a gripping instrument inserted into the morcellator shaft.

As can be seen from the sectional depiction shown in FIG. 2, in this embodiment two irrigation and/or suction canals 11 are positioned inside the optical observation unit 10, which is not shown in closer detail.

For insertion of the shaft 4 of the gripping instrument 2 equipped with the tool 6, the optical observation unit 10, and the at least one irrigation and/or suction canal 11, the morcellator 1 that can be operated by a handle 12 has a hollow cylindrical shaft 13 on whose distal end a cutting blade 14 is configured.

The gripping instrument 2 is positioned in the morcellator shaft 13 so that it is slidable in the longitudinal direction of the morcellator shaft 13 in such a way that the jaw members 6a of the tool 6 in a gripping position extend out of the morcellator shaft 13 on the distal side and are positioned in a resting position inside the morcellator shaft 13. The combination of the gripping instrument 2 and the morcellator 1 serves to grip with the gripping instrument 2 tissue that is to be morcellated and to pull it against the cutting blade 14 of the morcellator 1 that is preferably rotating around its longitudinal axis. The tissue morcellated in this manner can now be pulled by means of the gripping instrument 2 into the interior of the morcellator shaft 13 and completely removed by pulling the gripping instrument 2 out of the morcellator 1.

Because the gripping instrument 2 is additionally equipped with an optical observation unit 10, this optical observation unit 10 can simultaneously be used to observe and to guide the morcellation process. Especially in spatially restricted small operating areas, as for instance in the bladder, such a displacement of the optical observation unit 10 and additionally at least of one irrigation and/or suction canal 11 into the morcellator 1 is advantageous because additional processes for separate observation and irrigation-suction units are not possible in most cases.

An additional instrument equipped with a hollow shaft 15, such as for instance the resectoscope 3 shown in the illustration, serves to introduce into an operating area this arrangement of medical instruments consisting of the morcellator 1 and the gripping instrument 2 that can be inserted into the morcellator shaft 13.

Figure 3:
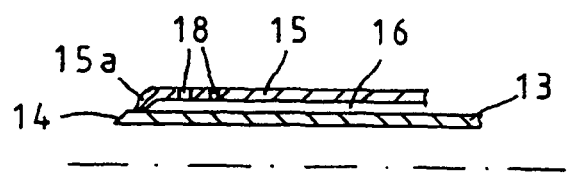
FIG. 3 shows an enlarged detailed longitudinal section along the section line III-III according to FIG. 1 through the resectoscope shaft with the morcellator shaft inserted, but without gripping instrument, depicting a first inventive embodiment.
Figure 4:
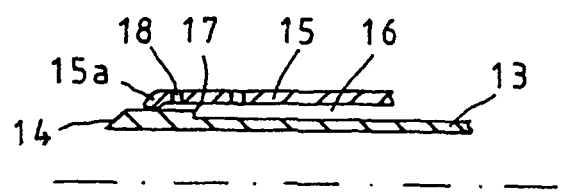
FIG. 4 shows a longitudinal section according to FIG. 3, but depicting the second inventive embodiment.

As can be seen from the sectional views in FIGS. 3 and 4, in the arrangement of the morcellator 1 inside the hollow shaft 15 of the additional instrument an additional irrigation and/or suction canal 16 serving mostly as a reverse flow canal that is free of any installations can be configured between the shaft 13 of the morcellator 1 and the inside of the hollow shaft 15 of the other medical instrument.

In the first embodiment depicted in FIG. 3, the distal end 15a of the hollow shaft 15 of the additional medical instrument is configured arched inward to configure the additional irrigation and/or suction canal 16.

According to the second embodiment depicted in FIG. 4, the shaft 13 of the morcellator 1 includes, at a distance from the distal-side cutting blade 14, a caliber indentation 17 that reduces the diameter of the shaft 13 to form the additional irrigation and/or suction canal 16.

Alternatively to these two illustrated embodiments it is also possible, for instance, to configure at least one longitudinal groove in the casing surface of the shaft 13 of the morcellator 1 to form the additional irrigation and/or suction canal 16.

To allow liquid to be diverted from the operating area by means of the additional irrigation and/or suction canal 16, in the distal area of the shaft 15 of the additional medical instrument suction openings 18 are configured by means of which, for instance, blood and/or irrigation liquid can be suctioned into the additional irrigation and/or suction canal 16.

To avoid a loss of pressure through the additional irrigation and/or suction canal 16, the additional irrigation and/or suction canal 16 on the proximal side is insulated by an insulation layer, in particular one of Teflon©, not shown in the illustration, which is in insulating contact with the inside of the hollow shaft 15 of the additional medical instrument.

Additional insulations, not shown in the illustration are provided to insulate the hollow shaft 13 of the morcellator 1 from the environment. This insulation occurs advantageously by means of a double insulation device, in such a way that preferably one insulation of the double insulating arrangement is configured as a ring insulation disc for insulation from the gripping instrument 2 that can be inserted into the shaft 13, and the other insulation of the double insulation arrangement is preferably configured as a cross-slit insulation that insulates the inner lumen of the shaft 13 when the gripping instrument 2 is withdrawn.

On inserting the morcellator 1 equipped with the gripping instrument 2 by means of the resectoscope 3 into the body of the patient, so that tissue that is not to be treated is not injured by the sharp cutting blade 14 of the morcellator 1, as soon as the morcellator 1 on the distal side extends out of the shaft 15 of the resectoscope 3, the shaft 4 of the gripping instrument 2 includes an outer diameter on the entire length of the shaft 4 which corresponds to the inner diameter of the morcellator shaft 3 on the cutting blade 14. Because of this form-locking contact of the shaft 4 on the inside of the cutting blade 14 and the at least flush locking of the shaft in the axial direction with the cutting blade 14, injuries can be prevented on inserting the morcellator 1 and the cutting blade 14 can be protected from possible damage.

Before insertion of the morcellator 1 into the operating area, the gripping instrument 2 must be inserted into the morcellator shaft 13, first in the axial direction, until on the distal side it is at least flush with the cutting blade 14 of the morcellator 1 in order to interrupt the cutting effect of the cutting blade 14. In this context, at least flush locking with the cutting blade 14 means that the distal end of the shaft 4 advantageously extends beyond the cutting blade 14 with a small overlap on the distal side, so that the cutting blade guard is improved. To ensure at all times the correct depth of insertion of the shaft 4 of the gripping instrument 2 into the morcellator shaft 13, so that the described cutting blade guard can become effective, it is further possible to configure on the morcellator 1 and/or on the gripping instrument 2 a stop which ensures the correct insertion depth when the instruments 1 and 2 are adjacent to one another.

To prevent the jaw members 6a of the tool 6, which works in the gripping position on the distal side outside of the morcellator shaft 13, from coming into contact with the cutting blade 14 of the morcellator shaft 13 and damaging it upon pulling the gripping tool 2 into the morcellator shaft 13, the angle of rotation of the jaw members 6a with respect to one another upon pulling the gripping tool 2 into the morcellator shaft 13 can be limited in such a way that the jaw members 6a of the tool 6 can be drawn, without contact, into the shaft 13.

A surgical instrument system configured in this way is distinguished in that, along with simple construction and versatility of applications, it allows the greatest possible cutting blade diameter of the morcellator 1 with simultaneous permanent visual control of the optical observation unit 10.

Figure 5:
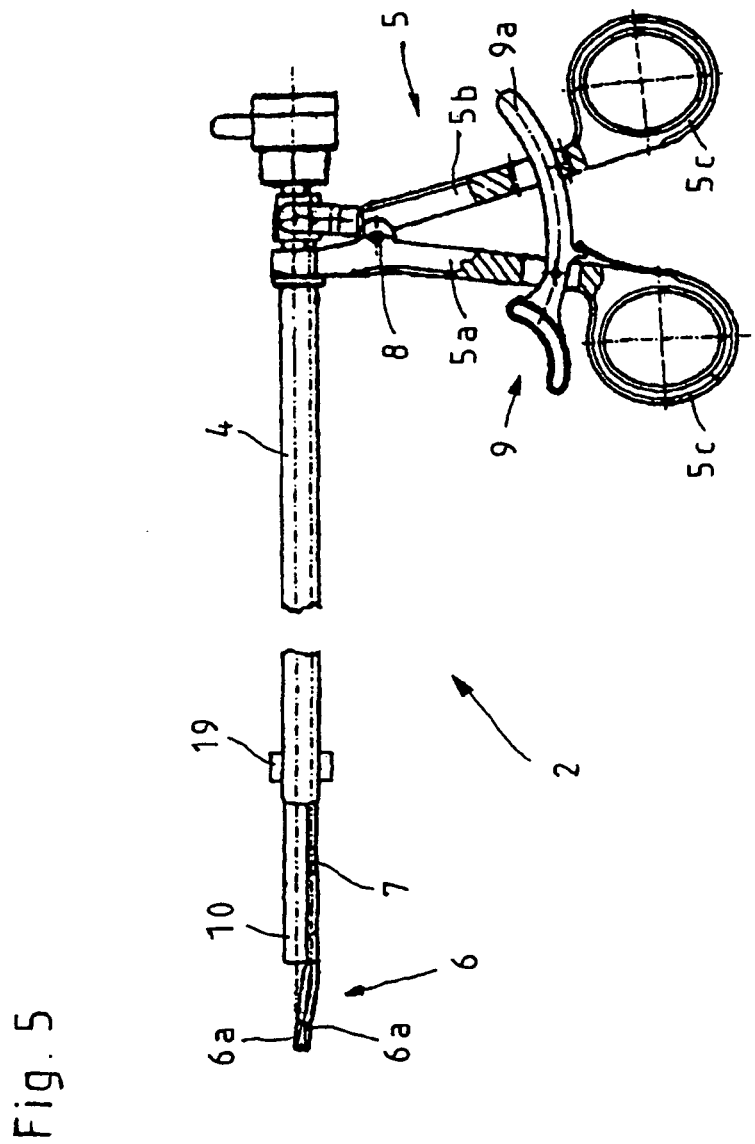
FIG. 5 shows a schematic side view of an alternative embodiment of a gripping instrument that can be inserted into an inventive surgical instrument system.

FIG. 5 shows an alternative embodiment of the gripping instrument 2 that can be inserted into the morcellator 1. This gripping instrument is distinguished from the gripping instrument depicted in FIG. 1 by the realization of the cutting blade guard. Upon insertion of the morcellator 1 equipped with the gripping instrument 2 by means of the resectoscope 3 into the patient's body, in order to prevent tissue that is not to be treated from being damaged by the sharp cutting blade 14 of the morcellator 1, as soon as the morcellator 1 on the distal side emerges from the shaft 15 of the resectoscope 3, in this alternative embodiment a cutting blade guard is configured as a thickened area 19 on the shaft 4 of the gripping instrument 2 and, at least on the cutting blade 14 of the morcellator 1, is in form-locking contact on the inside of the morcellator shaft 13. As a result of this form-locking contact on the inside of the cutting blade 4 and the at least flush locking of the thickened area 19 in the axial direction with the cutting blade 14, damage can be avoided upon inserting the morcellator 1.

In the illustrated embodiment the thickened area 19 on the proximal side is positioned at a distance from the tool 6 on the shaft 4 of the gripping instrument 2. Before inserting the morcellator 1 into the operating area, the gripping instrument 2 must thus, first in the axial direction, be introduced into the morcellator shaft 13 until the thickened area 19 on the distal side is locked at least flush with the cutting blade 14 of the morcellator 1, in order to halt the cutting effect of the cutting blade 14 and to provide protection against any possible damage.

What is claimed is:

1. A surgical instrument system comprising: a morcellator with a hollow shaft on whose distal end a cutting blade is configured,
   a gripping instrument with a shaft on whose distal end a tool is configured that comprises at least two jaw members and on whose proximal end a handle is configured that comprises at least two gripping members for activating the tool, wherein the gripping instrument is insertable into the hollow shaft of the morcellator by sliding it in a longitudinal direction of the hollow shaft of the morcellator,
   and an additional medical instrument, wherein the morcellator with the gripping instrument can be inserted into a hollow shaft of the additional medical instrument and in that at least one irrigation and/or suction canal is arranged within the hollow shaft of the morcellator and an additional irrigation and/or suction canal extends between an outer surface of the hollow shaft of the morcellator and an inner surface of the hollow shaft of the additional medical instrument such that the additional irrigation and/or suction canal is annular and is formed by the outer surface of the hollow shaft of the morcellator and the inner surface of the hollow shaft of the additional medical instrument, wherein a distal end of the hollow shaft of the additional medical instrument is arched inward about its complete circumference to configure the additional irrigation and/or suction canal.

2. The surgical instrument system according to claim 1, distinguished in that the additional irrigation and/or suction canal is insulated on a proximal side by an insulation from a inside of the hollow shaft of the additional medical instrument.

3. The surgical instrument system according to claim 1, distinguished in that the gripping instrument is outfitted additionally with an optical observation unit as well as at least one irrigation and/or suction canal, in such a way that the at least one irrigation and/or suction canal is positioned inside the optical observation unit.

4. The surgical instrument system according to claim 1, distinguished in that a cutting blade guard is configured on the gripping instrument and upon insertion of the morcellator into an operating area, the cutting blade guard can be brought into radially flush contact with the cutting blade of the morcellator and in the axial direction closes at least flush with the cutting blade.

5. The surgical instrument system according to claim 4, distinguished in that the cutting blade guard is configured as a thickened area positioned at a distance from the tool on the shaft of the gripping instrument.

6. The surgical instrument system according to claim 1, distinguished in that the gripping instrument is a gripping pincer equipped with two jaw members rotatable relative to one another.

7. The surgical instrument system according to claim 6, distinguished in that the jaw members can be fixed in their position with respect to one another by means of a sickle-shaped notching rod positioned on one of the gripping members.

8. The surgical instrument system according to claim 7, distinguished in that the jaw members can be fixed in pre-established angle positions with respect to one another.

9. The surgical instrument system according to claim 7, distinguished in that the jaw members are fixed with respect to one another by means of the handle.

10. The surgical instrument system according to claim 7, distinguished in that the jaw members are fixed with respect to one another by means of the jaw members.

11. The surgical instrument system according to claim 7, distinguished in that the jaw members are fixed with respect to one another by means of a push-pull rod that connects the handle with the jaw members.

12. The surgical instrument system according to claim 6, distinguished in that the angle of rotation of the jaw members with respect to one another upon pulling the gripping instrument into the hollow shaft of the morcellator can be restricted in such a way that the jaw members of the gripping instrument can be drawn into the shaft of the morcellator without making contact.

13. The surgical instrument system according to claim 1, distinguished in that the hollow shaft of the morcellator can be insulated from the environment by means of a double insulation arrangement.

14. A The surgical instrument system according to claim 13, distinguished in that one insulation of the double-insulation arrangement is configured as a ring insulation disc to insulate from the gripping instrument that can be inserted into the hollow shaft of the morcellator and the other insulation of the double insulation arrangement is configured as a cross-slit insulation, which insulates an inner lumen of the hollow shaft of the morcellator when the gripping instrument is withdrawn.

15. The surgical instrument system according to claim 1, distinguished in that the additional medical instrument is a resectoscope.

* * * * *